US00PP13142P2

(12) United States Plant Patent
Fear et al.

(10) Patent No.: US PP13,142 P2
(45) Date of Patent: Oct. 29, 2002

(54) PEACH TREE NAMED 'SUPECHTHIRTEEN'

(75) Inventors: Carlos D. Fear, Aptos; Bruce D. Mowrey, La Selva Beach; David W. Cain, Bakersfield, all of CA (US)

(73) Assignee: Sun World International, Inc., Bakersfield, CA (US)

( * ) Notice: Subject to any disclaimer, the term of this patent is extended or adjusted under 35 U.S.C. 154(b) by 0 days.

(21) Appl. No.: 09/792,970

(22) Filed: Feb. 26, 2001

(65) Prior Publication Data

US 2002/0120966 P1 Aug. 29, 2002

(51) Int. Cl.[7] ..... A01H 5/00
(52) U.S. Cl. ..... Plt./197
(58) Field of Search ..... Plt./197

*Primary Examiner*—Bruce R. Campell
*Assistant Examiner*—Susan B. McCormick
(74) *Attorney, Agent, or Firm*—Knobbe, Martens, Olson & Bear, LLP

(57) ABSTRACT

A new and distinct peach variety that possesses early-ripening fruit with delicate flavor, hardiness and a low winter chilling requirement.

1 Drawing Sheet

LATIN NAME OF THE GENUS AND SPECIES OF THE PLANT CLAIMED

*Prunus persica.*

VARIETY DENOMINATION

'Supechthirteen'.

BACKGROUND AND SUMMARY OF THE INVENTION

This invention relates to the discovery and asexual propagation of a new variety of clingstone peach, *Prunus persica* cv. 'Supechthirteen'. The new variety was first hybridized by Carlos D. Fear in May 13, 1991. The new variety was selected and evaluated by Bruce D. Mowrey and David W. Cain, near Wasco, Kern County, Calif., the variety being originated by hybridization. The new variety is characterized by its early-ripening fruit with delicate flavor, its hardiness, self-fertility, and its low winter chilling requirement.

The seed parent is 'Flordaprince' (unpatented) and the pollen parent is 'Earligrande' (unpatented). The parent varieties were first crossed in February 1989. The date of sowing was November 1989, with the date of first flowering being February 1991. The new peach variety was first asexually propagated by Bruce D. Mowrey in June 1991, near Wasco, Kern County, Calif. by budding onto Nemared rootstock.

The new peach variety 'Supechthirteen' may be distinguished from presently available low-chilling cultivars in commerce by the following combination of characteristics: the new peach variety cv. 'Supechthirteen' most nearly resembles 'Flordaprince'. It differs from 'Flordaprince' by ripening approximately 7 days before 'Flordaprince' and has more (80–100%) red overcolor compared to 'Flordaprince' (70–90%) and the red overcolor is more evenly distributed and less striped than with 'Flordaprince'. The new cultivar vaguely resembles 'Tropic Beauty' but ripens approximately 17 days before 'Tropic Beauty'.

The new peach cultivar, 'Supechthirteen' may be distinguished from its pollen parent 'Earligrande' (unpatented) in the following characteristics: the new cultivar ripens approximately 10 days before 'Earligrande'. The new cultivar has a lower winter chilling requirement, requiring approximately 150 hours of temperature below 45° F. vs 250 hours for 'Earligrande'. The new cultivar also has more (80–100%) external red blush than 'Earligrande' (40–60%).

The new peach variety cv. 'Supechthirteen' has been shown to maintain its distinguishing characteristics through successive asexual propagations, for example, by budding. The first propagation was performed near Wasco, Kern County, Calif. on June 1991 by Bruce D. Mowrey by budding onto Nemared rootstock.

BRIEF DESCRIPTION OF THE FIGURE

The accompanying drawing in FIG. 1 illustrates in full color.

DETAILED BOTANICAL DESCRIPTION OF THE INVENTION

Figure 1:
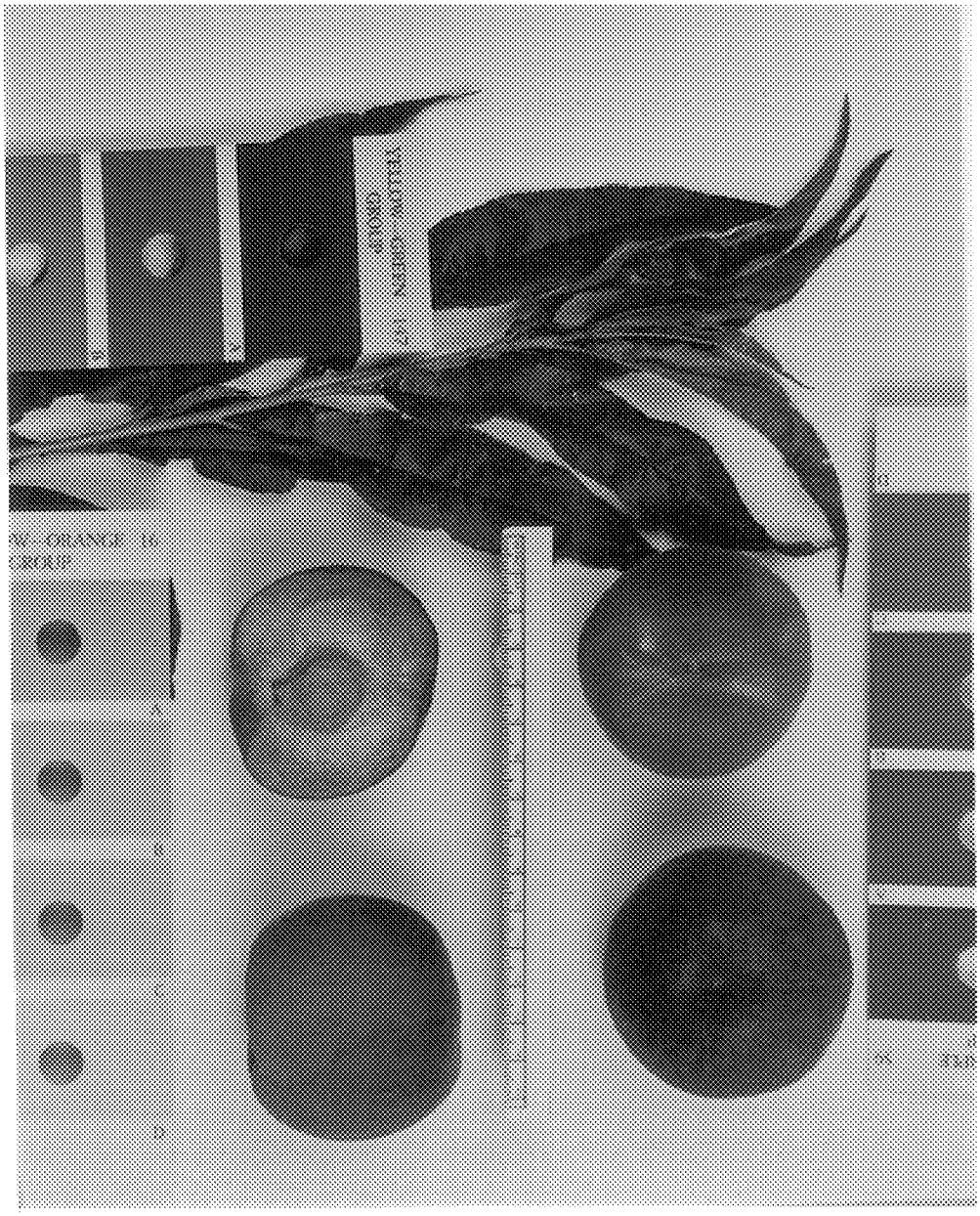

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England.

The descriptive matter which follows pertains to 'Supechthirteen' plants grown in the vicinity of Wasco, Kern County, Calif. with bloom and ripe dates also given for low chill sites near Mecca, Riverside County, Calif., during 2000, and is believed to apply to plants of the variety grown under similar conditions of soil and climate elsewhere:

TREE

General: Trees were three years old and were maintained at a height of about ten feet and a canopy diameter of about ten feet by annual prunings.

*Size.*—Medium.

*Vigor.*—Typical of the species; shoot growth on mature tree during one growing season is about 600 to 1000 mm (growth rate responds typically to irrigation, fertilization, rootstock, and other cultural factors).
*Habit.*—Semi-upright.
*Density of foliage.*—Medium.
*Shape.*—Vase formed.
*Hardiness.*—Hardy near Wasco, Calif.
*Productivity.*—Medium productive.
*Fruit bearing.*—Regular bearer.
*Root stock.*—Nemared.

Trunk: Trunk is round in outline and of medium circumference, averaging 60 cm at 30 cm above ground level on 3-year-old trees.
*Surface texture.*—Smooth — medium.
*Color.*—About Grey-Brown group 199B.

Branches: Branches are round in outline and average 20 cm in circumference on 3-year-old trees as measured 30 cm distal from the branch juncture with the trunk.
*Shape.*—Medium — slender.
*Color.*—About 175C to 201D, varying with age of tree.
*Surface texture.*—Smooth — medium.
*Surface appearance.*—Semi-glossy — dull.

Lenticels:
*Number.*—Medium — few.
*Size.*—Large — medium.
*Color.*—About greyed-orange 161A.
*Density.*—1.6 /cm$^2$.

LEAVES

General:
*Average length.*—15.3 cm.
*Average width.*—3.4 cm.
*Size.*—Medium.
*Outline.*—Lanceolate.
*Profile.*—Up folded.
*Leaf blade tip.*—*Curved downwardly.*
*Angle of tip.*—*Acute.*
*Margin.*—Finely serrate.
*Undulation of margin.*—Slight.
*Apex.*—Acuminate.
*Base.*—V-shaped.
*Thickness.*—Medium.
*Venation.*—Pinnately net veined.
*Vein color.*—Yellow-green 147C.

Upper surface:
*Color.*—About Yellow-Green group 147A.
*Glossiness.*—Medium.
*Pubescense.*—Absent.
*Surface texture.*—Rugose.
*Surface appearance.*—Semi-glossy.

Lower surface:
*Color.*—About Yellow-Green group 147B.
*Glossiness.*—Weak.
*Pubescense.*—Absent.
*Surface texture.*—*Rugose.*
*Surface appearance.*—Dull.

Petiole:
*Length.*—Medium — short, about 1.1 cm.
*Thickness.*—Medium, about 2 mm.
*Color.*—About yellow-green 147C.

Glands:
*Average number.*—4.3.
*Positioning.*—On both leaf base and petiole.
*Size.*—About 0.9 mm long by 0.7 mm wide.
*Shape.*—Reniform.
*Color.*—About Yellow-Green group 153D.

Stipules:
*Persistence.*—Fall off.

Wood (leaf) buds:
*Shape.*—Ovoid.
*Size.*—About 1.1 mm wide at widest point, by about 3 mm long (for a typical 5 mm diameter shoot).
*Position relative to shoot.*—Adpressed.
*Support.*—Decurrent.
*Time of bud burst.*—Bud burst occurs at the time of flower bud expansion.

Flowering shoots:
*Anthocyanin coloration.*—Present.
*Intensity.*—Medium.
*Thickness.*—Thin — medium, about 0.4 cm.
*Internode length.*—Medium, about 1.7 cm, midway on flowering shoots.
*Density of buds.*—Medium.
*Distribution.*—On one-year-old shoots.
*Ratio of wood (leaf) buds to flowering shoots.*—1:2.

FLOWERS

Flower-buds:
*Hardiness.*—Hardy in central California.
*Size.*—About 4 mm long by about 3 mm wide at widest point (for a typical 5 mm diameter shoot).
*Length.*—Medium.
*Shape.*—Plump.
*Positioning.*—Free.
*Pubescence.*—Pubescent.
*Color.*—About Greyed-Orange group 165A.

General:
*Date of first bloom.*—Jan. 25, 2000 at low chill site in Riverside County, near Mecca, Calif. Feb. 3, 2000 at medium high chill site in Wasco, Kern County, Calif.
*Date of full bloom.*—Jan. 30, 2000 at low chill site in Riverside County, near Mecca, Calif.; Feb. 8, 2000 at medium high chill site in Wasco, Kern County, Calif.
*Time of bloom.*—Medium, as compared with similar low chill varieties in the growing area of Wasco, Kern County and Mecca, Riverside County, Calif.
*Duration of bloom.*—Medium, about 10 days.
*Size (diameter of the fully open flower).*—Small, about 2.6 cm.
*Shape.*—Campanulate.
*Petals.*—Free.
*Color (fully opened flower).*—About 62B.

Peduncle:
*Length.*—About 4 mm.
*Width.*—About 3 mm.
*Pubescence.*—Absent.

Receptacle:
*Depth.*—Medium.
*Pubescence of inner surface (at pink bud stage).*—Pubescent.
*Pubescence of outer surface.*—Absent.

Sepals:
*Number per flower.*—5.
*Positioning.*—Adpressed to petals.
*Shape.*—Elliptic.
*Width at first opening of flower.*—About 6 mm.
*Color at first opening of flower.*—About yellow-green 145A with highlights of red 46A.
*Pubescence of inner surface.*—Absent.
*Pubescence of outer surface.*—Pubescent.
*Frequency of flowers with double sepals.*—None.

Petals:
*Number of petals per typical flower.*—5.
*Frequency of flowers with double petals.*—*None.*
*Size.*—Small, about 0.7 cm in width.
*Shape.*—Elliptical.
*Claw length.*—Short.
*Margin waviness.*—Absent.
*Shape of apex.*—Rounded.
*Shape of base.*—Petal narrows at point of attachment.
*Base angle.*—Medium.
*Texture.*—Smooth.
*Margin.*—Entire (smooth).
*Pubescence of inner surface.*—Absent.
*Pubescence of outer surface.*—Absent.
*Color* (*inner surface*).—About 62B.
*Color* (*outer surface*).—About 62B.

Stigma:
*Position* (*as compared with anthers*).—Level.

Anthers:
*Color* (*just before dehiscence*).—About Red 39A on outer edges and about Yellow 14B in recesses.

Pollen:
*Color.*—About 14C.

Stamens:
*Position.*—Perigynous.

Pistil:
*Frequency of supplementary pistils.*—Few.
*Number.*—Sometimes more than one. (varies from 1–2).
*Length when flower bud first opens.*—About 18 mm.
*Color.*—About 150D.

Ovary:
*Pubescence.*—Pubescent.
*Density of hairs.*—Dense.

Style:
*Pubescence* (*of base*).—Medium.
*Density of hairs.*—Medium.

FRUIT

General:
*Maturity when described.*—*Firm, ripe.*
*Date.*—Apr. 8, 2000 at the low-chill site near Mecca, Riverside County, Calif.; May 2, 2000 at the medium-high chill site near Wasco, Kern County, Calif.
*Size.*—Medium, about 6 cm, about 120 g.
*Axial diameter.*—About 6 cm.
*Transverse in suture plane.*—6.5 cm.
*At right angles to suture plane.*—6 cm.
*Form.*—Uniform, rounded, and slightly flattened toward tip. Tip tends to be slightly recessed.
*Position of maximum diameter.*—Towards middle.
*Symmetry about the suture.*—Symmetric.
*Season ripening.*—Early.
*Use.*—Fresh market.
*Keeping quality.*—Medium.
*Resistance to.*—Insects: good. Diseases: good. Shipping quality: held firm in cold storage for 2 weeks at 38°–42° F. without internal breakdown of flesh or appreciable loss of eating quality.

Suture: An inconspicuous line extending from base to apex along one side.

Ventral surface:
*Shape.*—Rounded slightly.
*Lips.*—Equal.
*Depression of apex.*—Indistinct.
*Pistil base.*—Not persisting.
*Pubescence at apex.*—Moderate to scant; hairs short.
*Density of apex pubescence.*—Medium.

Stem cavity:
*Shape.*—Flaring, circular; with suture showing on one side.
*Depth.*—1.3 cm.
*Breadth.*—2.8 cm.

Base:
*Shape.*—Rounded.

Apex:
*Shape.*—Slightly depressed.

Pistil point:
*Shape.*—Slightly depressed.

Stem:
*Length.*—0.8 cm, stout, glabrous.
*Diameter.*—About 3.2 mm.
*Color.*—About yellow-green 148B.
*Adherence to stone.*—Strong.

Skin:
*Thickness.*—Medium.
*Texture at harvest.*—Smooth and crisp.
*Reticulation.*—Absent.
*Roughness.*—Absent.
*Tenacity.*—Tenacious to flesh.
*Tendency to crack.*—None in wet season.
*Color.*—Ground color: 8C; Overcolor: 59A.
*Down* (*pubescence*).—Moderate to scant, short.

Flesh:
*Color.*—Near skin: about Red-Purple 59B; Near pit: about Yellow 8B.
*Amygdalin.*—Wanting.
*Juice.*—Moderate.
*Sugar content.*—Low to medium.
*Texture.*—Medium, coarse, melting.
*Fibers.*—Abundant, coarse.
*Ripens.*—Earliest at apex.
*Flavor.*—Delicate.
*Eating quality.*—Fair — good for early season fruit.
*Stone/flesh ratio.*—1 cm diameter/3.2 cm diameter.

STONE

General:
*Adherence to flesh.*—Cling, adheres to flesh over entire surface.
*Fibers.*—Long.
*Size.*—Medium — small.
*Length.*—2.4 cm.
*Width along suture plane.*—2.3 cm.
*Width at right angle to suture plane.*—1.8 cm.
*Width of stalk end.*—0.4 cm.
*Angle of stalk end.*—Obtuse.
*Form* (*profile*).—Oval.
*Form* (*ventral view*).—Globular.
*Base.*—Oblique.
*Hilum.*—Oval.
*Apex.*—Pointed.
*Position of maximum breadth.*—Middle.
*Sides.*—Equal.
*Surface.*—Regularly furrowed near base; pitted throughout.
*Outgrowing keel.*—Partly developed.

*Ridges.*—Rounded towards base.
*Pits.*—Elongated.
*Ventrical edge.*—Thin with slight wing toward base.
*Dorsal edge.*—Narrow.
*Color of stone.*—About Greyed-Orange 165D.
*Tendency to split.*—Slight in wet season.
*Kernel size* (*when dried*).—About 10 mm wide by about 13 mm long.
*Kernel color.*—About yellow-orange 18C.
*Kernel astringency.*—Very bitter.
*Kernel shape.*—Oval.
*Amygdalin.*—Undetected.

Supechthirteen: Table of R.H.S. Color Codes:

| | | R.H.S. Color Code |
|---|---|---|
| TREE: | Trunk: | 199B |
| LEAVES: | Upper Surface: | 147A |
| | Lower Surface: | 147B |
| | Glands: | 153D |

-continued

Supechthirteen: Table of R.H.S. Color Codes:

| | | | R.H.S. Color Code |
|---|---|---|---|
| FLOWERS: | Flower Buds: | | 165A |
| | General: | Fully opened flower: | 62B |
| | Petals: | Inner surface: | 62B |
| | | Outer Surface: | 62B |
| | Anthers: | Outer edges | 39A |
| | | Recesses just before dehiscence: | 14B |
| | Pollen: | | 14C |
| FRUIT: | Skin: | Ground color: | 8C |
| | | Overcolor: | 59A |
| | Flesh: | Near skin: | 59B |
| | | Near pit: | 8B |
| STONE: | | Stone color: | 165D |

What is claimed is:

1. A new and distinct peach tree as herein described and illustrated.

* * * * *